(12) United States Patent
Sudo et al.

(10) Patent No.: US 7,678,055 B2
(45) Date of Patent: Mar. 16, 2010

(54) ULTRASONIC PROBE WITH A CONDUCTIVE SUBSTRATE CONNECTED TO A TRANSDUCER

(75) Inventors: Masaaki Sudo, Yokohama (JP); Susumu Hiki, Otawara (JP); Shinichi Sato, Nasu-gun (JP); Taihei Sato, Nasu-gun (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 866 days.

(21) Appl. No.: 10/784,187

(22) Filed: Feb. 24, 2004

(65) Prior Publication Data

US 2004/0167405 A1    Aug. 26, 2004

(30) Foreign Application Priority Data

Feb. 24, 2003   (JP) .............................. 2003-046515

(51) Int. Cl.
*A61B 8/00* (2006.01)
(52) U.S. Cl. .................. 600/459; 600/437; 367/157; 367/189; 73/584; 73/596
(58) Field of Classification Search .......... 600/437, 600/459; 367/140, 157, 180, 189; 73/584, 73/596
See application file for complete search history.

(56) References Cited

U.S. PATENT DOCUMENTS

| 3,952,387 | A |   | 4/1976  | Iinuma et al. |         |
|-----------|---|---|---------|---------------|---------|
| 5,295,487 | A |   | 3/1994  | Saitoh et al. |         |
| 5,402,791 | A | * | 4/1995  | Saitoh et al. | 600/459 |
| 6,162,178 | A | * | 12/2000 | Garcia et al. | 600/459 |
| 6,238,481 | B1|   | 5/2001  | Yamashita et al. |      |

FOREIGN PATENT DOCUMENTS

| JP | 59-160305   | 9/1984  |
|----|-------------|---------|
| JP | 61-75700    | 4/1986  |
| JP | 4-284800    | 10/1992 |
| JP | 5-23341     | 2/1993  |
| JP | 11-164397   | 6/1996  |
| JP | 11-226012   | 8/1999  |
| JP | 2002-217057 | 8/2002  |
| JP | 2002-232996 | 8/2002  |

\* cited by examiner

*Primary Examiner*—Brian Casler
*Assistant Examiner*—Parikha S Mehta
(74) *Attorney, Agent, or Firm*—Oblon, Spivak, McClelland, Maier & Neustadt, L.L.P.

(57) ABSTRACT

A piezoelectric transducer for sending and receiving an ultrasonic wave and an FPC for applying current to the piezoelectric transducer is provided, the FPC is arranged oppositely to a side face of the piezoelectric transducer, and a soldering material for electrically connecting the piezoelectric transducer to the FPC is arranged in a corner portion formed by the piezoelectric transducer and the FPC.

10 Claims, 12 Drawing Sheets

ULTRASONIC PROBE WITH A CONDUCTIVE SUBSTRATE CONNECTED TO A TRANSDUCER

CROSS-REFERENCE TO RELATED APPLICATIONS

This application is based upon and claims the benefit of priority from the prior Japanese Patent Application No. 2003-46515, filed Feb. 24, 2003, the entire contents of which are incorporated herein by reference.

BACKGROUND OF THE INVENTION

1. Field of the Invention

The present invention relates to an ultrasonic probe for sending and receiving an ultrasonic wave and a method for fabricating the probe.

2. Description of the Related Art

For example, ultrasonic diagnostic equipment has been used in medical diagnosis or industrial diagnosis, in which a lesion in the body or a crack in piping is detected by sending an ultrasonic wave to a diagnostic object such as the human body or piping and receiving a reflected wave of the ultrasonic wave. The ultrasonic diagnostic equipment comprises a main body of the equipment and an ultrasonic probe for sending and receiving the ultrasonic wave.

Figure 14:
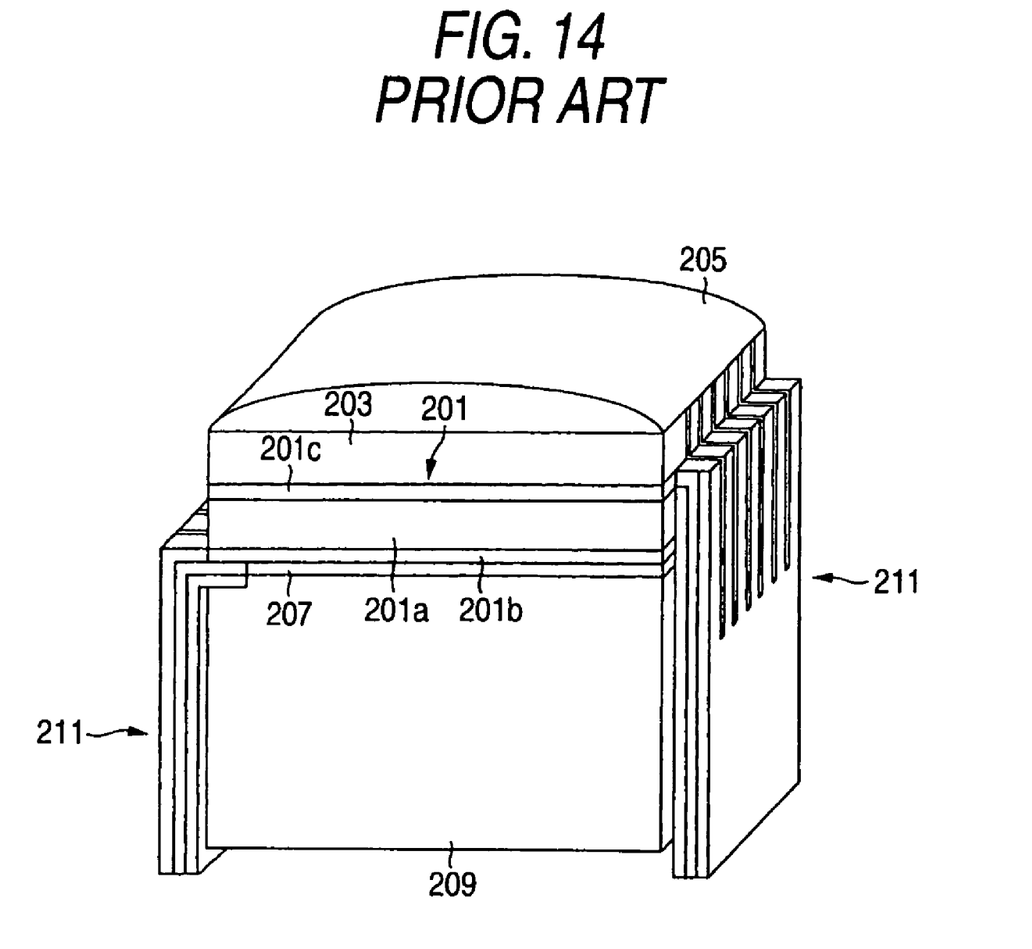
FIG. 14 is a perspective view showing the conventional ultrasonic probe.
Figure 15:
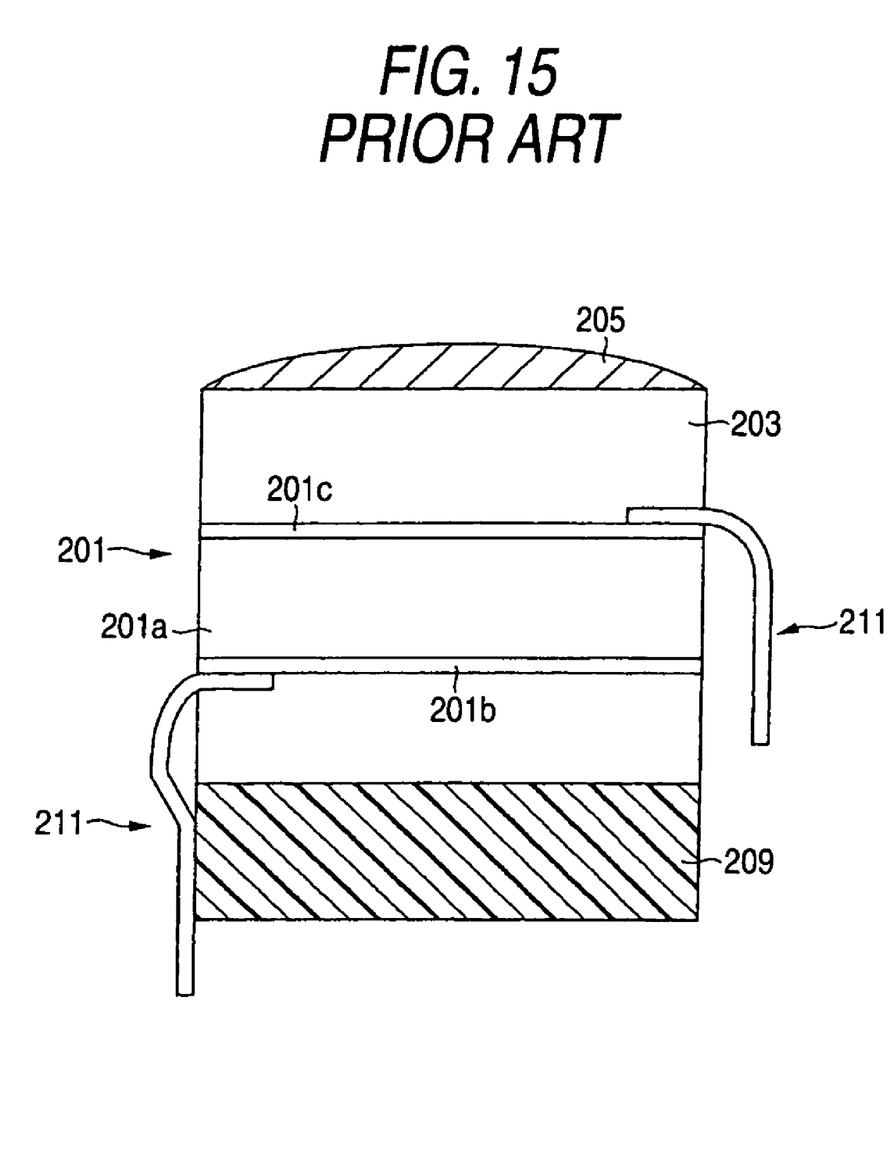
FIG. 15 is a cross sectional view showing the conventional ultrasonic probe.

FIG. 14 and FIG. 15 show a configuration of a conventional ultrasonic probe of ultrasonic diagnostic equipment for medical application. As shown in FIG. 14, the ultrasonic probe has a piezoelectric transducer 201. The piezoelectric transducer 201 is formed into a rectangular, piezoelectric element by dicing a platelike piezoelectric ceramic.

An audio matching layer 203 for matching audio impedance is provided at an earth electrode 201c side of the piezoelectric transducer 201, and in turn an audio lens 205 is provided on a surface of the audio matching layer 203. A backing material 209 comprising rubber having a good sound absorption performance is jointed to a signal electrode 201b side of the piezoelectric transducer 201 through epoxy based resin 207.

On both side faces of the piezoelectric transducer 201, flexible printed circuits 211 (FPCs) are disposed such that they are opposed to each other. Each of end portions of the FPCs 211 is connected to the signal electrode 201b or earth electrode 201c of the piezoelectric transducer 201 through a soldering material.

As shown in FIG. 15, the FPCs 211 are bended at approximately 90 degrees in the vicinity of the connected portion to the piezoelectric transducer 201, and a rear anchor portions of the FPCs are connected to a main body (not shown) of the ultrasonic diagnostic equipment disposed at a backing material 209 side.

When the ultrasonic probe having the above configuration is used, first an audio lens 205 is contacted to a diagnosis object. Then, an electrical signal is applied to the piezoelectric transducer 201 through the FPCs 211, thereby an ultrasonic wave is generated from the piezoelectric transducer 201. The generated ultrasonic wave is sent to the diagnosis object through the audio lens 205, and reflected within the diagnosis object, and then received by the piezoelectric transducer 201. The received ultrasonic wave is converted to an electric signal in the piezoelectric transducer 201, and transferred to the main body of the ultrasonic diagnostic equipment through the FPCs 211.

In such configured ultrasonic probe, the FPCs 211 are bent at approximately 90 degrees in the vicinity of the jointed portion with the piezoelectric transducer 201. According to the finite deflection theory, bending stress exerted on the curved portions of the FPCs 211 exceeds 100 N/mm$^2$, therefore the jointed portions of the FPCs 211 with the piezoelectric transducer 201 were easily broken due to the bending stress exerted on the curved portions of the FPCs 211. Particularly, in dicing, large machining stress is applied to the jointed portions of the FPCs 211 with the piezoelectric transducer 201, therefore the jointed portions were still further easily broken.

Thus, a configuration in which the FPCs are connected to the piezoelectric transducer without being curved by projecting an end portion of the piezoelectric transducer from an end face of the backing material has been developed. In the ultrasonic probe, the FPCs are arranged along the end face of the backing material, and the end portions of the FPCs are jointed with the earth electrode formed on a bottom of the projected end of the piezoelectric transducer.

However, when the end portion of the piezoelectric transducer is projected from the end face of the backing material, there is a problem that a structure having the projected portion floating in the air is formed, and thus the crack is easily occurred in the piezoelectric material due to the machining stress generated in the dicing. Since the crack in the piezoelectric material has a great influence to the ultrasonic characteristics, in recent years, dicing without damaging the piezoelectric material has been required.

BRIEF SUMMARY OF THE INVENTION

The invention, which was made in view of the above circumstances, aims to provide an ultrasonic probe that can restrain breakdown of the piezoelectric material and improve the jointed strength of the piezoelectric transducer with a conductive substrate, and provide a method for fabricating the probe.

To solve the above problems and achieve the objects, the ultrasonic probe and the method for fabricating the probe of the invention are configured as follows.

A piezoelectric transducer for sending and receiving the ultrasonic wave and a conductive substrate for applying current to the piezoelectric transducer are provided, the conductive substrate is arranged oppositely to a side face of the piezoelectric transducer, and a conductive material that electrically connects the piezoelectric transducer to the conductive substrate is arranged in a corner portion formed by the piezoelectric transducer and the conductive substrate.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
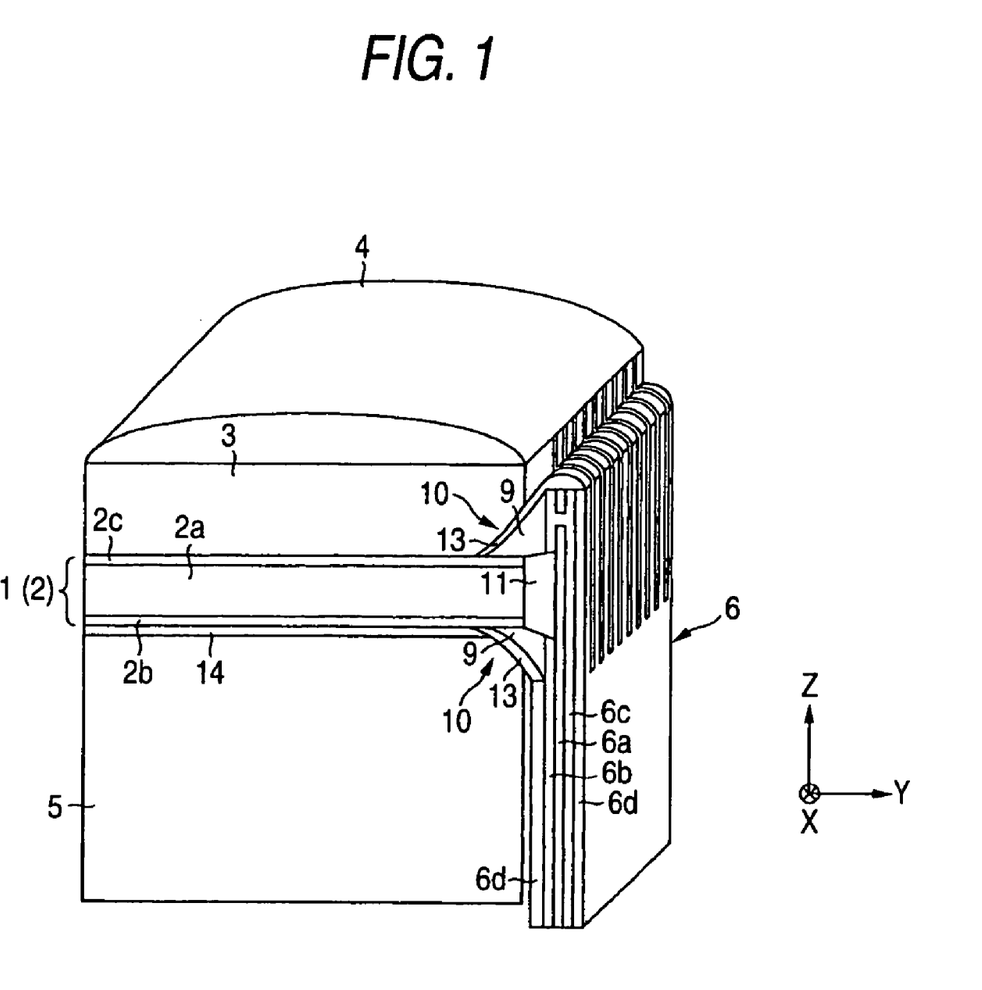
FIG. 1 is a perspective view showing a configuration of an ultrasonic probe according to the first embodiment of the invention.
Figure 2:
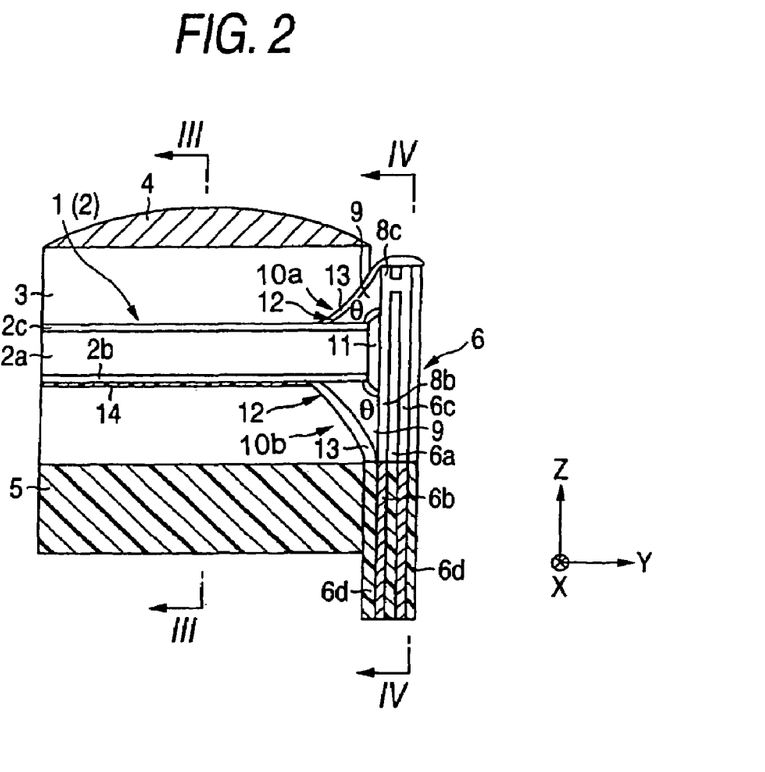
FIG. 2 is a cross sectional view showing the configuration of the ultrasonic probe according to the embodiment.
Figure 3:
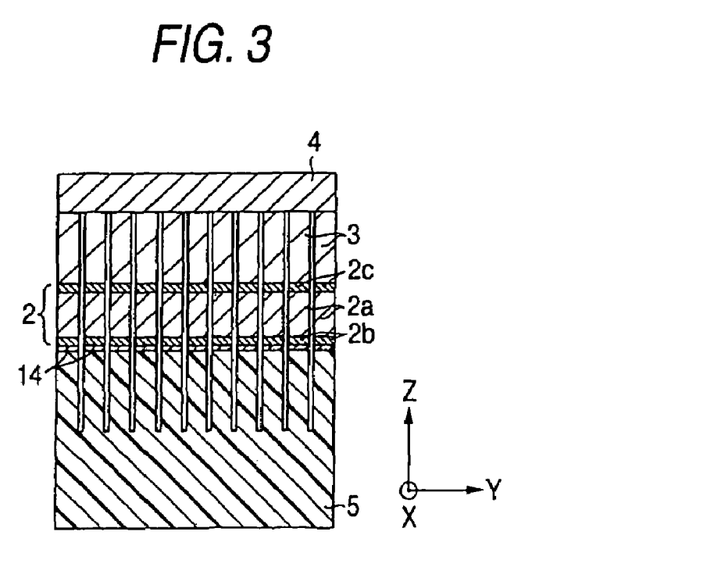
FIG. 3 is a cross sectional view cut along the line A-A in FIG. 2, showing the configuration of the ultrasonic probe according to the embodiment.
Figure 4:
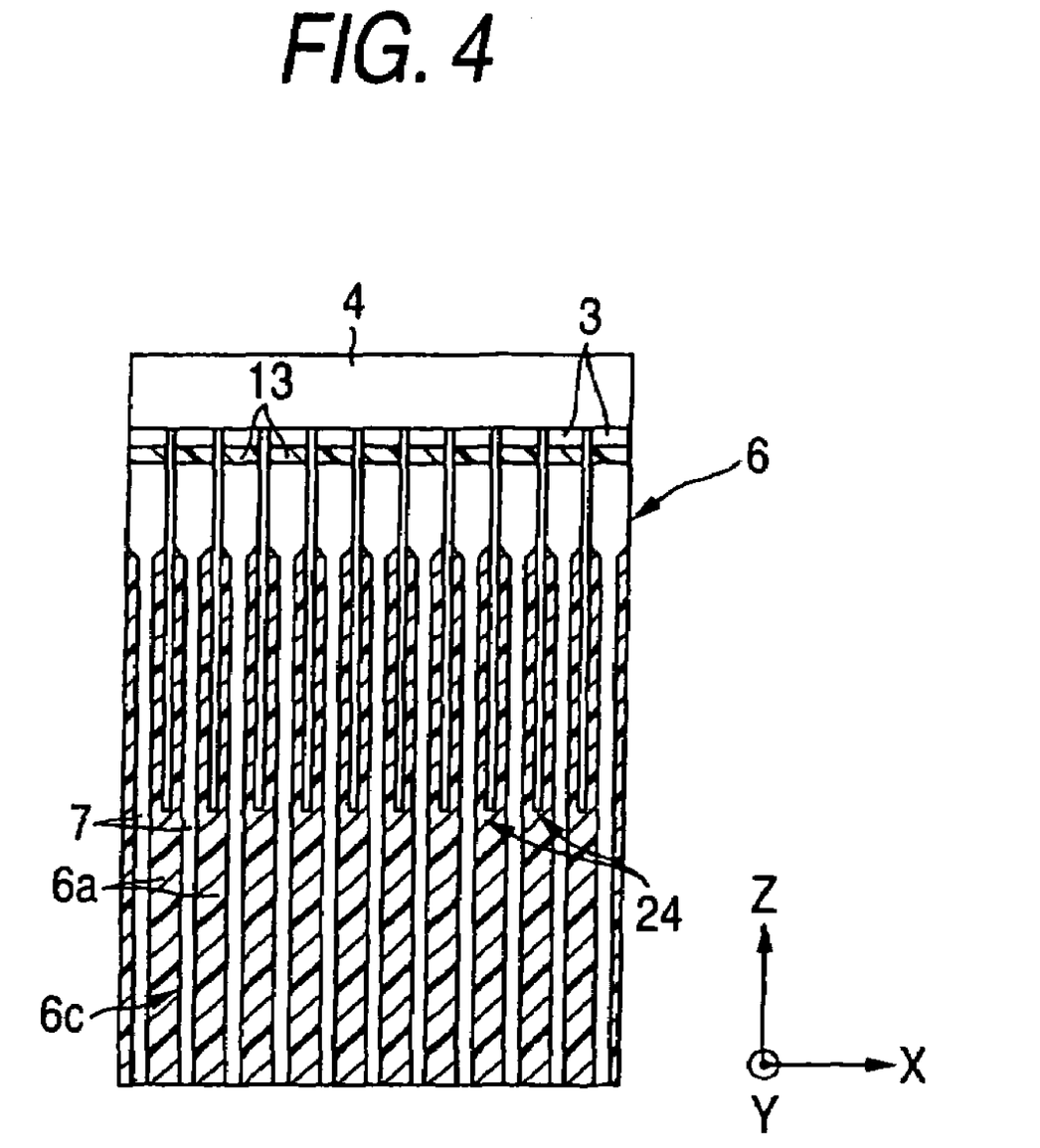
FIG. 4 is a cross sectional view cut along the line B-B in FIG. 2, showing the configuration of the ultrasonic probe according to the embodiment.

Hereinafter, the first embodiment of the invention is described with reference to FIG. 1 to FIG. 8. FIG. 1 is a perspective view showing a configuration of an ultrasonic probe according to the first embodiment of the invention; FIG. 2 is a cross sectional view showing the configuration of the ultrasonic probe according to the embodiment; FIG. 3 is a cross sectional view cut along the line III-III in FIG. 2 showing the configuration of the ultrasonic probe according to the embodiment; and FIG. 4 is a cross sectional view cut along the line IV-IV in FIG. 2.

The ultrasonic probe shown in FIG. 1 and FIG. 2 has a piezoelectric transducer 1. The piezoelectric transducer 1 has a rectangular solid shape, and respective three edges of the shape are corresponding to the three directions of x, y, and z which are perpendicular to each together.

As shown in FIG. 3, the piezoelectric transducer 1 comprises a large number of (for example, 128 to 256), strip-shaped piezoelectric elements 2 arranged with a predetermined interval along the X direction (only eleven elements are shown).

Each of the piezoelectric elements 2 has a piezoelectric material 2a, an earth electrode 2c (first electrode), and a signal electrode 2b (second electrode), and each of the signal electrode 2b and earth electrode 2c is provided on either end of the piezoelectric material 2a in the z direction. On a surface of the earth electrode 2c, an audio matching layer 3 for matching audio impedance is provided.

As a material for the piezoelectric material 2a, ceramics of lead zirconate titanate (PZT), PZNT single crystal comprising solid solution of lead zinc-niobate and lead titanate, or PZMT single crystal comprising solid solution of lead magnesium-niobate and lead titanate is used. As a material for the signal electrode 2b and earth electrode 2c, a good conductor such as gold or silver is used. As a material for the audio matching layer 3, glass or resin is used.

As shown in FIG. 1 and FIG. 2, at an earth electrode 2c side of the piezoelectric transducer 1, an audio lens 4 is provided through the audio matching layer 3. At a signal electrode 2b side of the piezoelectric transducer 1, a block-like backing material 5 is jointed through epoxy-based resin 14. As a material for the backing material 5, the rubber having the good sound absorption performance is used.

On one side face of the piezoelectric transducer 1 in the y direction, an FPC 6 (conductive substrate) is provided substantially perpendicular to the y direction, or provided such that composition angle, θ, is approximately 90 degrees. The FPC 6 has a signal wiring 6b and an earth wiring 6c insulated from each other through an insulating layer 6a, and an outside of the FPC is covered by a cover material 6d made of an insulating material. Each of the wirings 6b and 6c has electrical paths 7 of which the number is corresponding to number of the above piezoelectric elements 2 (refer to FIG. 4).

End portions of the electrical paths 7 of respective wirings 6b, 6c are exposed from the cover material 6d of the FPC 6 to a piezoelectric transducer 1 side as a signal wiring electrode 8b and an earth wiring electrode 8c. Interval between the signal wiring electrode 8b and earth wiring electrode 8c is approximately equal to the size of the piezoelectric transducer 1 in the z direction, and each of the signal wiring electrode 8b and the earth wiring electrode 8c is positioned at either side of the piezoelectric transducer 1 in the z direction.

A soldering material 9 (conductive material) is arranged in corner portions 10a, 10b formed by the piezoelectric transducer 1 and the FPC 6. The soldering material 9 at the first corner 10a positioned at the earth electrode 2c side electrically connects the earth wiring electrode 8c to the earth electrode 2c, and the soldering material 9 at the second corner 10b positioned at the signal electrode 2b side electrically connects the signal wiring electrode 8b to the signal electrode 2b.

A fillet is formed in the peripheral region of a soldering material 12. The fillet generates a tensile stress, which is stronger than a sharing stress, on a jointed surface with the piezoelectric transducer 1 or FPC 6, and thus improves jointing strength on the jointed surface. The soldering material 12 is coated by a nonconductive resin material 13 (nonconductive material) in order to protect the surface of the material 9.

Nonconductive adhesive 11 (nonconductive material) for insulating the signal electrode 2b from the earth electrode 2c is interposed between the piezoelectric transducer 1 and FPC 6. The nonconductive adhesive 11 acts to temporarily fix the piezoelectric transducer 1 to the FPC 6 in fabrication process of the ultrasonic probe as described later.

A rear anchor portion of the FPC 6 is connected to a main body of ultrasonic diagnostic equipment (not shown) disposed at a backing material 5 side through a connector (not shown).

When the configured ultrasonic probe is used, first the audio lens 4 is contacted to a diagnosis object. Then, an electric signal is applied from the main body of the ultrasonic diagnostic equipment to the piezoelectric transducer 1 through the signal wiring 6b and the earth wiring 6c, so that an ultrasonic wave is generated from the piezoelectric transducer 1. The generated ultrasonic wave is sent to the diagnosis object through the audio lens 4, and reflected within the diagnosis object, and then received by the piezoelectric transducer 1. The received ultrasonic wave is converted to an electric signal by the piezoelectric transducer 1, and then transferred to the main body of the ultrasonic diagnostic equipment through the signal wiring 6b and the earth wiring 6c.

Figure 5A:
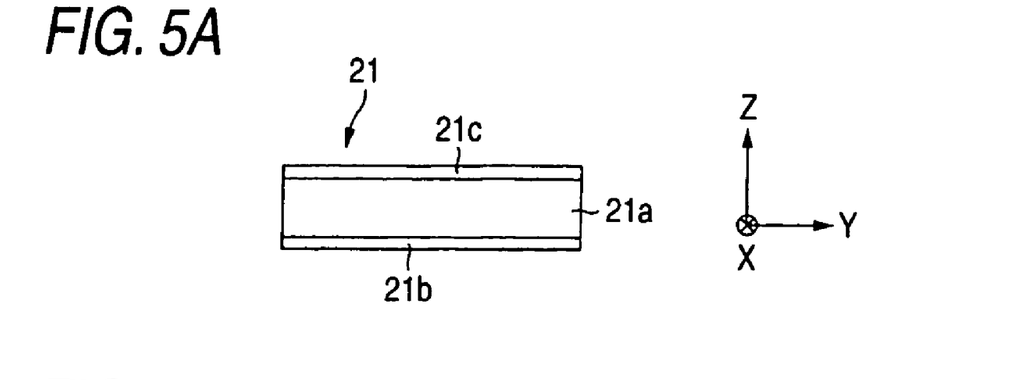
FIG. 5A to FIG. 5C are process views showing a fabrication process of the ultrasonic probe according to the embodiment.
Figure 5B:
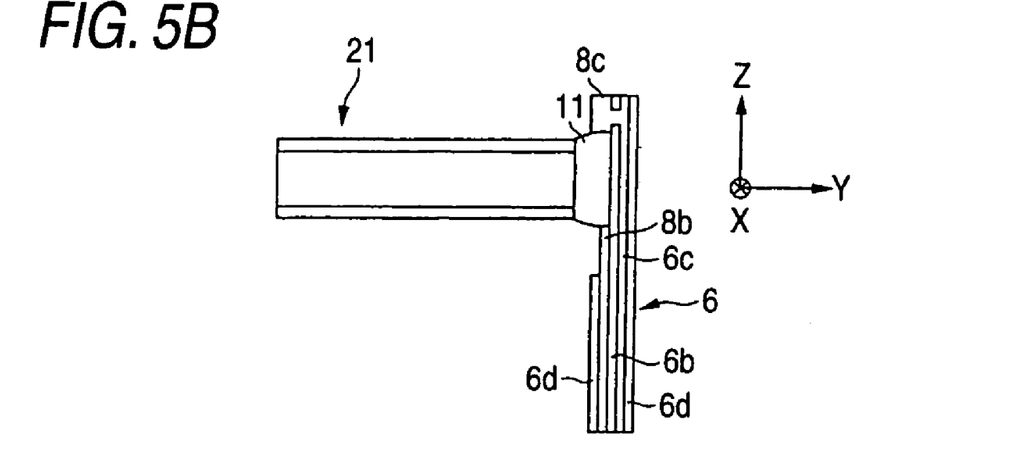
Figure 5C:
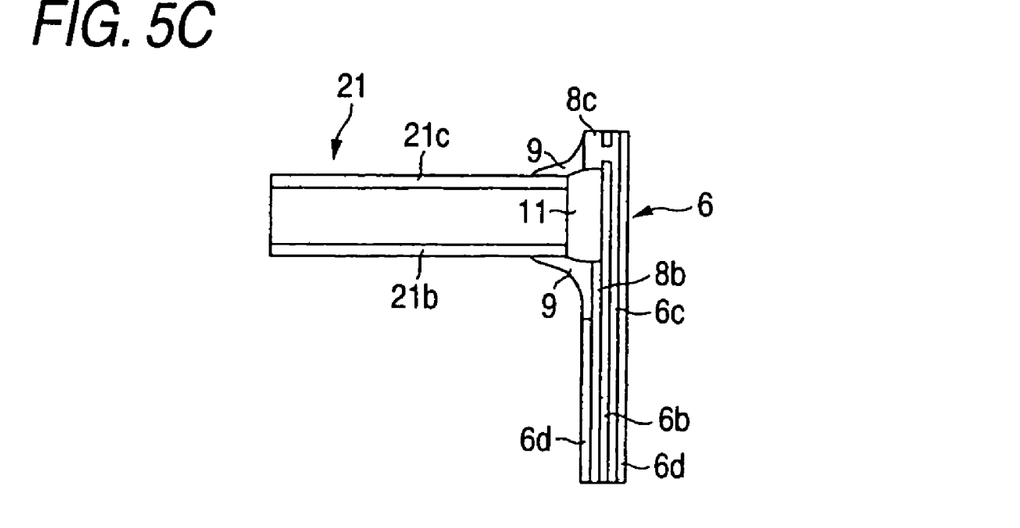
Figure 6A:
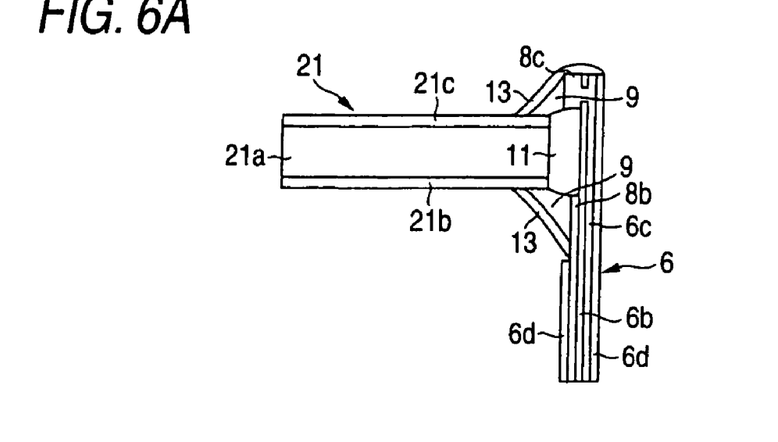
FIG. 6A to FIG. 6C are process views showing the fabrication process of the ultrasonic probe according to the embodiment.
Figure 6B:
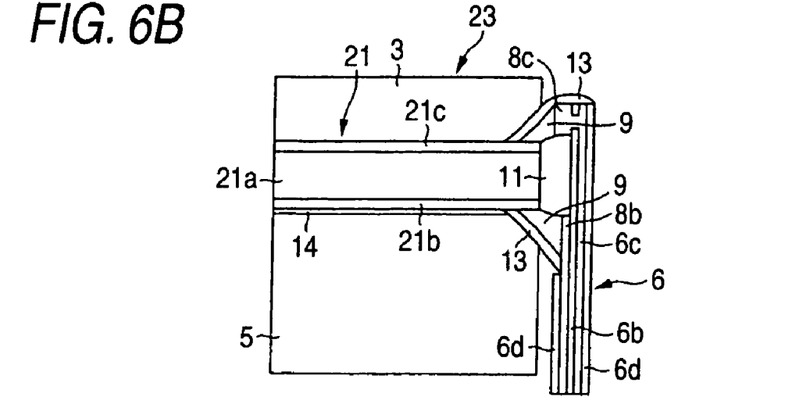
Figure 6C:
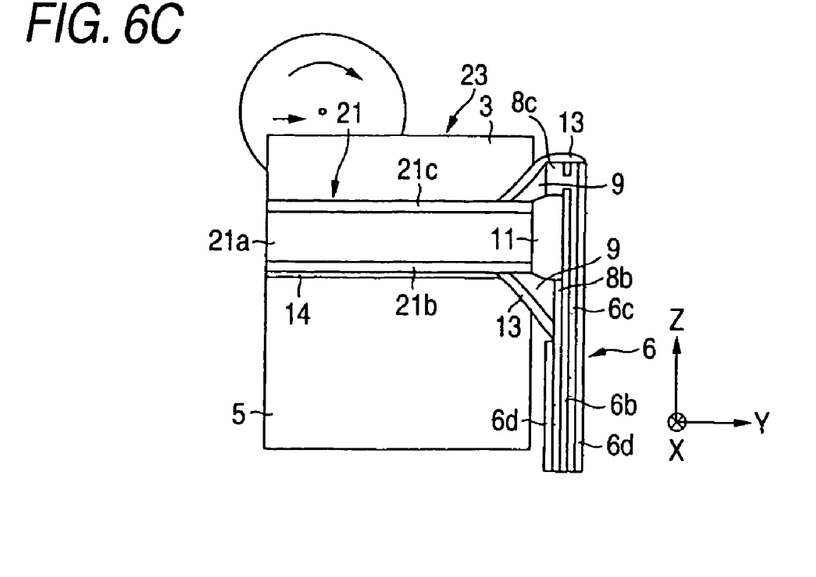
Figure 7A:
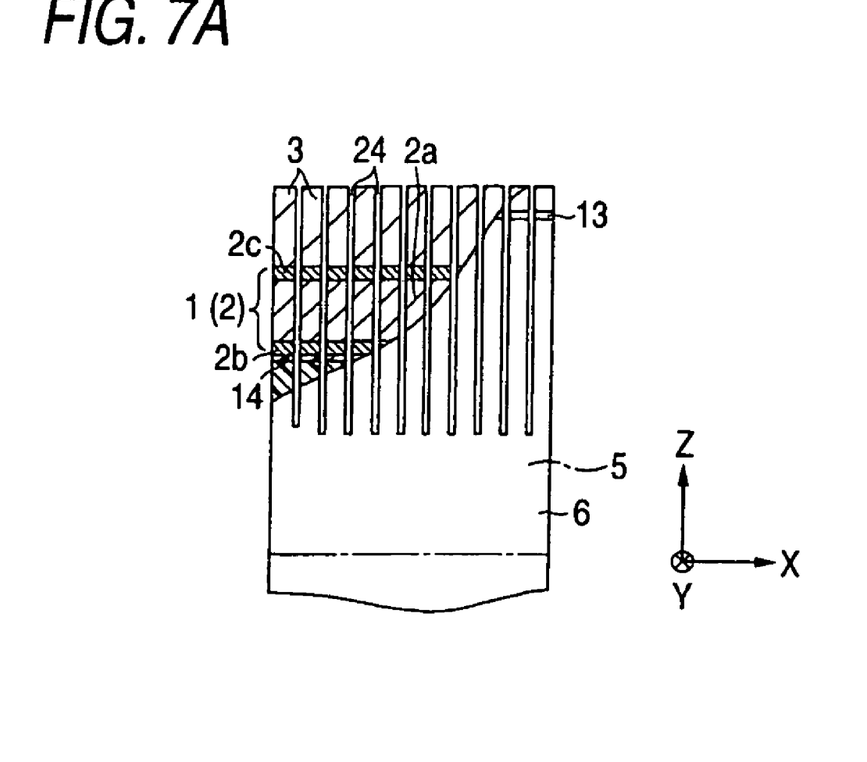
FIG. 7A and FIG. 7B are process views showing the fabrication process of the ultrasonic probe according to the embodiment.
Figure 7B:
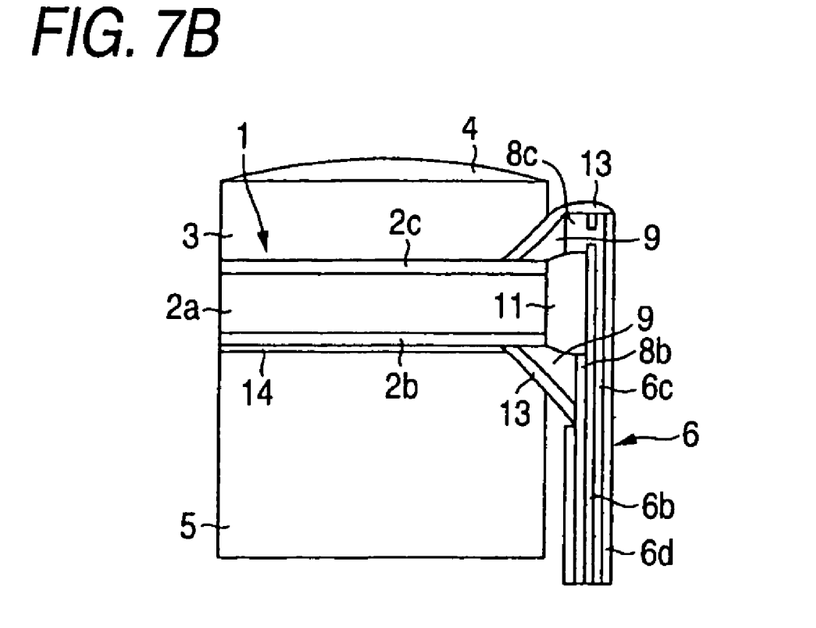
Figure 8:
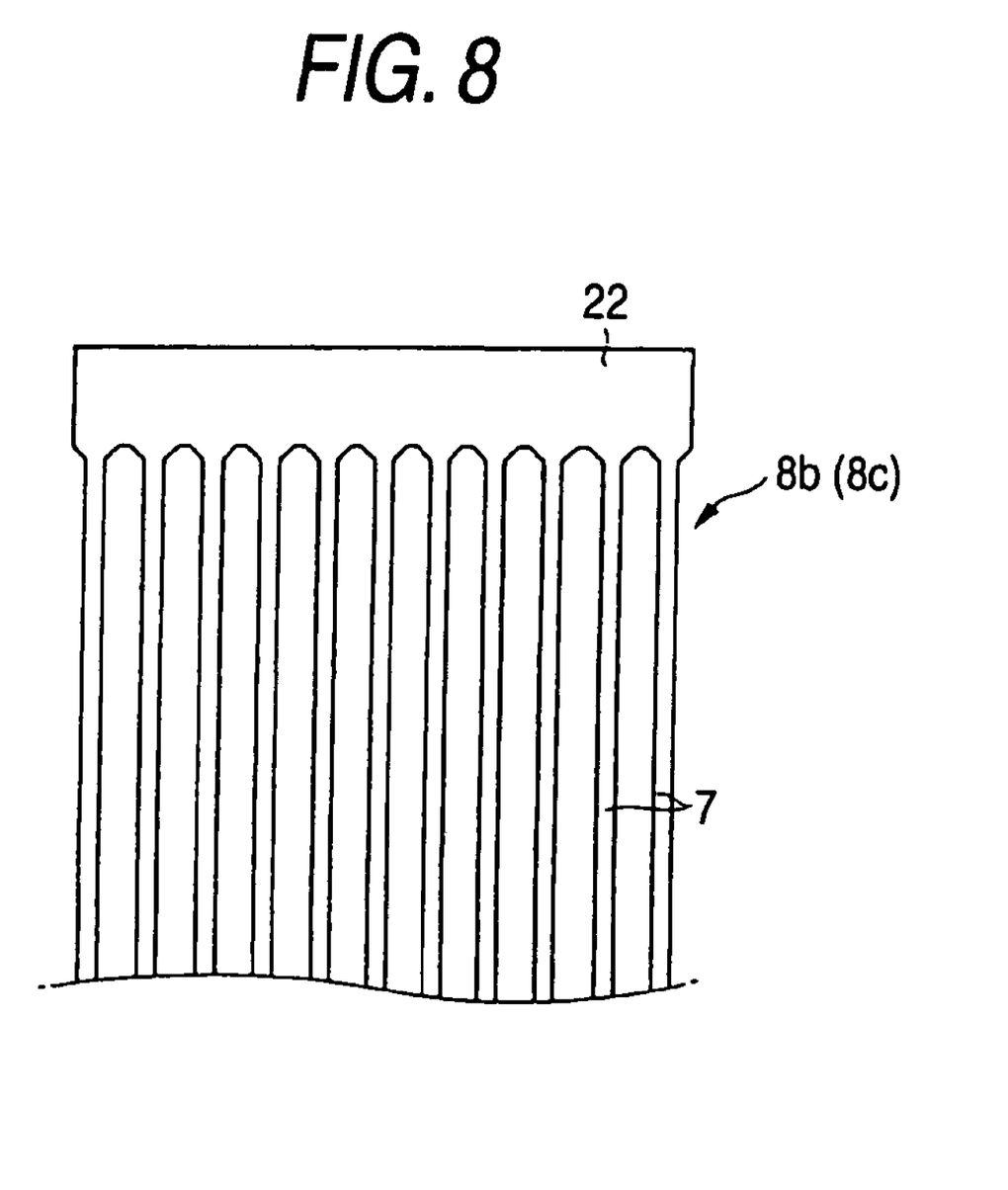
FIG. 8 is a schematic view showing a pattern of signal and earth wirings before dicing according to the embodiment.

Next, a method for fabricating the configured ultrasonic probe is described using FIG. 5 to FIG. 7.

As shown in FIG. 5A, a piezoelectric transducer before being separated 21 is prepared. The piezoelectric transducer before being separated 21 has a rectangular-solid-like piezoelectric material 21a. The three edges of the piezoelectric material 21a are in correspondence with the x, y, and z directions, and metallic thin films 21b, 21c such as gold or silver film are formed on both faces in the z direction.

Next, as shown in FIG. 5B, the FPC 6 is disposed approximately perpendicular to the y direction on one side face of the piezoelectric transducer before being separated 21 in the y direction, and then the piezoelectric transducer before being separated 21 is temporarily fixed to the FPC 6 by the nonconductive adhesive 11.

Next, as shown in FIG. 5C, the soldering material 9 is supplied to the corner portion 10 formed by the piezoelectric transducer before being separated 21 and the FPC 6, and the metallic thin film 21b is welded to the signal wiring electrode 8b using a contact type heat tool (heating unit) such as a soldering iron, as well as the metallic thin film 21c is welded to the earth wiring electrode 8c.

Thereby, the metallic thin film 21b is electrically connected to the signal wiring electrode 8b, as well as the metallic thin film 21c is electrically connected to the earth wiring electrode 8c. In this condition, the signal wiring electrode 8b and the earth wiring electrode 8c are electrically communicated through a flat portion 22 (refer to FIG. 8).

For heating the soldering material 9, a noncontact type heater tool including laser irradiation or infrared ray irradiation can be used in addition to the contact type heat tool such as the soldering iron. Also, soldering cream or conductive adhesive can be used instead of the soldering material 9. When the soldering cream is used, atmosphere heating is generally carried out; however, if the heating temperature is not less than Curie point of the piezoelectric material 21a, depolarization occurs in the piezoelectric material 21a, therefore repolarization treatment needs to be performed in subsequent processes. When the conductive adhesive is used, hardening by atmosphere heating as in the soldering cream or photo-reactive hardening by ultraviolet ray irradiation is performed.

Next as shown in FIG. 6A, the surface of the soldering material 9 is coated by the nonconductive resin material 13 in order to prevent the jointed portions 12 of the signal electrode 21b with the signal wiring electrode 8b and the earth electrode with the earth wiring electrode 8c.

Next, as shown in FIG. 6B, the audio matching layer 3 is jointed with the surface of the metallic thin film 21c, and then the block-like backing material 5 is jointed with the surface of the metallic thin film 21b through the epoxy-based resin 14.

Through the above processes, a layer structure 23 comprising the audio matching layer 3, metallic thin film 21c, piezoelectric material 21a, metallic thin film 21b, and backing material 5 is formed.

Next, as shown in FIG. 6C, a large number of grooves 24 are provided in the layer structure 23 using a dicing machine (dicing). The groove portions 24 are formed such that they extend from the audio matching layer 3 side to the backing material 5.

Thereby, the piezoelectric transducer before being separated 21 comprising the piezoelectric material 21a and the metallic thin films 21b, 21c are formed into the above piezoelectric transducer 1 comprising a large number of strip-shaped piezoelectric elements 2 as shown in FIG. 7A.

At that time, the flat end portion 22 of the FPC 6 connected to the metallic thin films 21b, 21c is also cut and divided by the dicing machine, thereby respective piezoelectric elements 2 are electrically communicated to respective electric paths 7 independently.

Finally, as shown in FIG. 7B, the audio lens 4 is provided on the surface of the audio matching layer 3. That is the end of the fabrication process of the ultrasonic probe.

According to the above configured ultrasonic probe and the method for fabricating the probe, the FPC 6 is disposed substantially perpendicular to the y direction on one side face of the piezoelectric transducer 1 in the y direction, and the corner portion 10 formed by the piezoelectric transducer 1 and the FPC 6 is supplied with the soldering material 9, thereby the signal electrode 2b is electrically connected to the signal wiring electrode 8b, as well as the earth electrode 2c is electrically connected to the earth wiring electrode 8c.

Therefore, since the piezoelectric transducer 1 can be connected to the FPC 6 without necessity of bending the FPC 6, and the connected portion 12 is not applied with the unnecessary load, the jointed strength of the piezoelectric transducer 1 with the FPC 6 is improved.

Since the corner portion 10 formed by the piezoelectric transducer 1 and the FPC 6 has an angle of approximately 90 degrees, the fillet is easily formed by the soldering material 9 supplied to the corner portion 10. Since the fillet improves breaking tolerance on a jointed face with the piezoelectric transducer 1 or the FPC 6, the jointing strength of the piezoelectric transducer 1 with the FPC 6 can be improved.

Furthermore, as described above, since the jointed strength of the piezoelectric transducer 1 with the FPC 6 is improved, damage to the jointed portion 12 due to the machining stress exerted on the jointed portion 12 in the dicing can be restrained.

The FPC 6 having the signal wiring 8b and the earth wiring 8c is also used as the conductive substrate.

Thus, since electrical current can be applied to the piezoelectric transducer 1 using only one FPC 6, the component cost can be reduced.

Furthermore, the nonconductive adhesive 11 is interposed between the piezoelectric transducer 1 and FPC 6.

Thus, since the signal side and earth side of the piezoelectric transducer 1 are isolated from each other by the nonconductive adhesive 11, operation of supplying the soldering material 9 to the corner portion 10 formed by the piezoelectric transducer 1 and the FPC 6 can be easily carried out.

The soldering material 9 supplied to the corner portion 10 is coated by the nonconductive resin material 13 in order to protect the material 9 from the ambient air or moisture.

Thus, since the soldering material 9 becomes hard to deteriorate, reduction of the jointed strength of the piezoelectric transducer 1 with the FPC 6 can be suppressed.

Next, the second embodiment of the invention is described with reference to FIG. 9.

Figure 9:
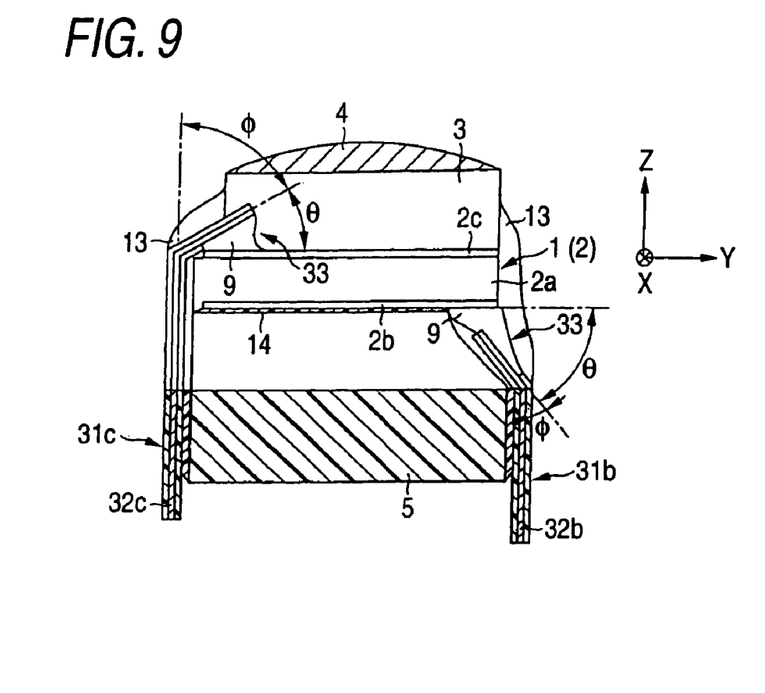
FIG. 9 is a cross sectional view showing a configuration of an ultrasonic probe according to the second embodiment of the invention.

FIG. 9 is a cross sectional view showing a configuration of the ultrasonic probe according to the second embodiment of the invention. In a description of the embodiment, the same components as in the first embodiment are marked with the same symbols and explanation for the components is omitted.

As shown in FIG. 9, in the ultrasonic probe according to the embodiment, FPCs 31b, 31c are provided on both sides of the piezoelectric transducer 1 in the y direction respectively. Each of the FPCs 31b, 31c has a signal wiring 32b and an earth wiring 32c, and each of the signal wiring 32b and the earth wiring 32c has electric paths 7 of which the number is corresponding to the number of the piezoelectric elements 2.

Respective end portions of the FPCs 31b, 31c are bended at a bending angle, φ, to the piezoelectric transducer 1 side, and corner portions 33 of which the composition angle is θ are formed between the piezoelectric transducer 1 and the FPCs 32b, 32c. Although the composition angle, θ, can be within a range from 5 degrees to 90 degrees, preferably, it is 10 degrees to 90 degrees.

The soldering material 9 is supplied to the corner portions 33 formed by the piezoelectric transducer 1 and the FPCs 31b, 31c. The soldering material 9 electrically connects the earth electrode 2c to the earth wiring 32c, and the signal electrode 2b to the signal wiring 32b.

In the configured ultrasonic probe, the FPCs 31b, 31c for applying current to the piezoelectric transducer 1 are disposed at both sides of the piezoelectric transducer 1 in the y direction, and end portions of the FPCs that are connected to the piezoelectric transducer 1 are bended to the piezoelectric transducer 1 side.

Thus, since bending stress exerted on curved portions of the FPCs 31b, 31c can be made small, load applied to the jointed portions of the piezoelectric transducer 1 with the FPCs 31b, 31c is reduced. Thereby, jointed strength of the piezoelectric transducer 1 with the FPCs 31b, 31c is improved.

Furthermore, since the composition angle, θ, of the corner portions 33 is made to be 5 degrees or more, the fillet is easily formed by the supplied soldering material 9.

Thus, according to the same principle as in the first embodiment, the jointed strength of the piezoelectric transducer 1 with the FPCs 31b, 31c is improved.

Next, a peeling strength evaluation test and a dicing tolerance test are described. The peeling strength evaluation test and the dicing tolerance test are conducted to clear effects of the fillet on the jointed strength of the piezoelectric transducer 1 with the FPC 6.

Figure 10:
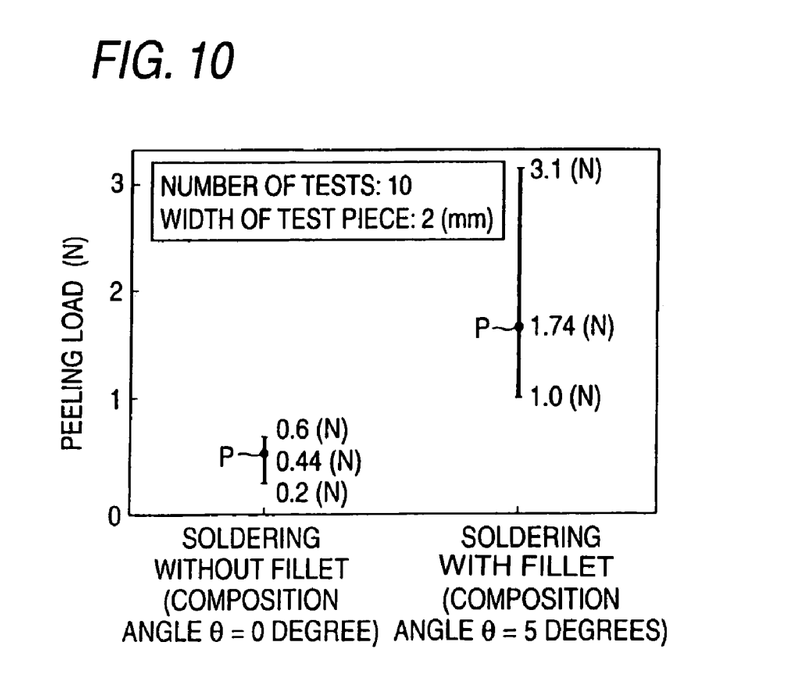
FIG. 10 is a graph showing results of a peeling strength evaluation test.

FIG. 10 shows results of the peeling strength evaluation test. In FIG. 10, points P indicate the average peeling load, and upper and lower ends of lines extending vertically from the points P indicate the maximum and minimum values of the peeling load respectively.

In the peeling strength evaluation test, the peeling load required for peeling the FPC that is jointed by soldering with a piezoelectric transducer from the piezoelectric transducer was measured. Test pieces with and without the fillet formed in the jointed portion 12 of the piezoelectric transducer 1 with the FPC were prepared ten pieces each.

The test conditions are as follows:
width of the test piece: approximately 2 mm;
number of tests: 10;
composition angle of the corner portion θ: 5 degrees.

As shown in FIG. 10, the average peeling load in the case without forming the fillet in the jointed portion was 0.44 N. On the other hand, the average peeling load in the case with forming the fillet in the jointed portion was 1.74 N. That is, it was found that the average peeling load in the case with forming the fillet was improved to almost quadruple of that in the case without forming the fillet.

Accordingly, it was confirmed from the peeling strength evaluation test that the jointed strength of the piezoelectric transducer with the FPC was drastically improved by forming the fillet in the jointed portion in jointing the piezoelectric transducer with the FPC.

The inventors still conducted the peeling strength evaluation test in the case that the composition angle, θ, was 10 degrees and confirmed that further large effects were obtained.

Figure 11A:
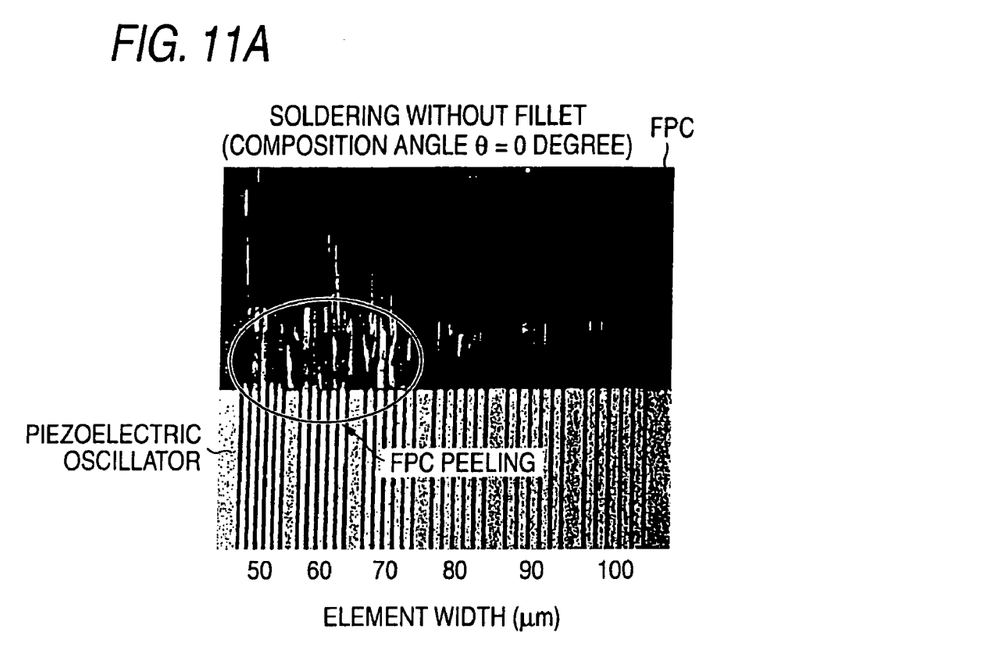
FIG. 11 is a photograph showing results of a dicing tolerance test, where A is a case when a fillet is not formed in a jointed portion and B is a case when the filet is formed in the jointed portion.
Figure 11B:
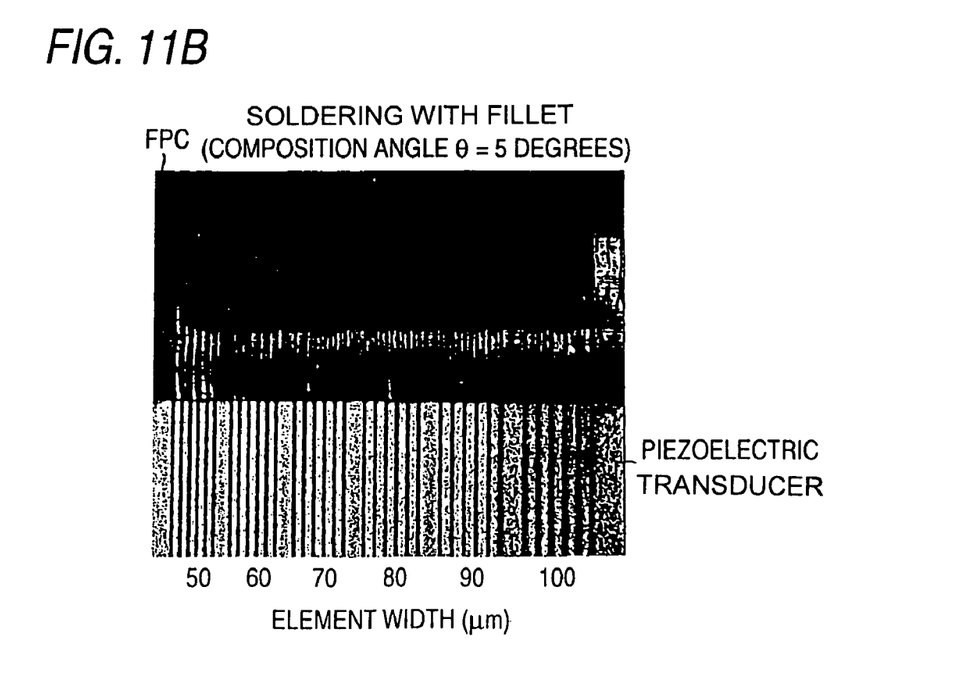

FIGS. 11A and 11B show results of the dicing tolerance test.

In the dicing tolerance test, element width was measured when the FPC jointed by soldering with the piezoelectric transducer was peeled from the piezoelectric transducer with cutting pitch being narrowed by 1 mm every sixth dicing. Test pieces with and without the fillet formed in the jointed portion of the piezoelectric transducer with the FPC were prepared respectively.

The test conditions are as follows:
rotational frequency of blade: 30000 rpm;
blade width: 0.05 mm;
cutting pitch: 0.15 mm to 0.10 mm;
element width: 0.1 mm to 0.05 mm.

As shown in FIGS. 11A, 11B, when the fillet was not formed in the jointed portion, peeling was occurred at an element width of 0.07 mm. On the other hand, when the fillet was formed in the jointed portion, peeling was not found even at an element width of 0.05 mm.

Accordingly, it was confirmed that when the piezoelectric transducer was jointed with the FPC in the dicing tolerance test, the peeling of the FPC from the piezoelectric transducer due to the machining stress applied in dicing was restrained by forming the fillet in the jointed portion.

The inventors still conducted the dicing tolerance test in the case that the composition angle, θ, was 10 degrees and confirmed that further large effects were obtained.

Next, numerical comparison of the bending stress exerted on the FPC to that in the related art is described. In this numerical comparison, an FPC having a stacked structure of polyimide/Cu/polyimide was used.

The calculation conditions (related art) are as follows:
radius of curvature, R, of FPC: 5 mm;
bending angle, φ: 90 degrees;
thickness of Cu, t: 0.025 mm;
and Young's modulus, E, of Cu: 130000 N/mm$^2$.

The maximum value of the bending stress, σ, exerted on the curved portion is expressed with the following numerical formula 1 according to the functional relation between stress and strain.

(The numerical formula 1 is inserted here.)

As shown in the numerical formula 1, when the FPC is bended at the above conditions, the maximum value of the bending stress, σ, exerted on the curved portion is approximately 325 N/mm$^2$.

On the other hand, in the ultrasonic probe according to the first embodiment, it is found that the bending stress is zero because of the structure where the FPC is not bended, and the bending stress is drastically decreased compared with the related art.

Also, in the ultrasonic probe according to the second embodiment, it is found that the bending stress is decreased compared with the related art because the bending angle, φ, is less than 90 degrees.

Figure 12:
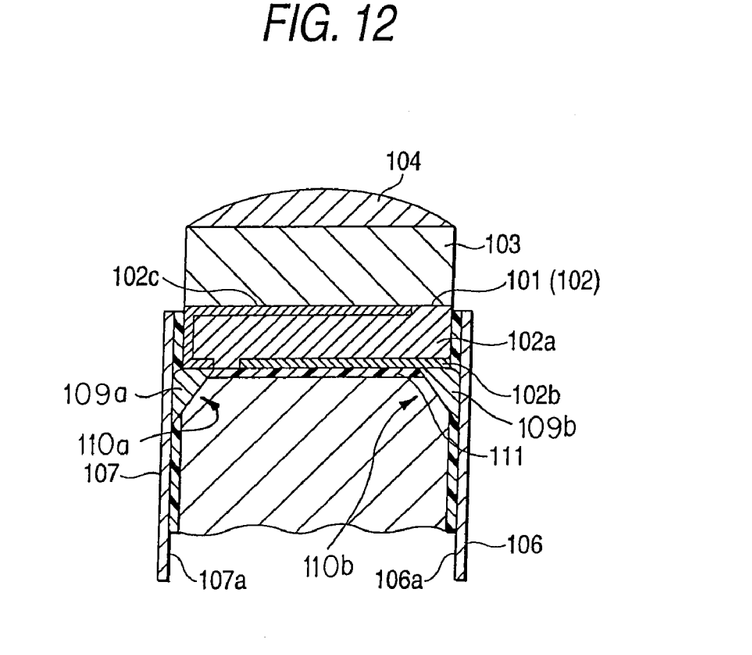
FIG. 12 is a cross sectional view showing a configuration of an ultrasonic probe according to the third embodiment of the invention.

FIG. 12 is a cross sectional view showing a configuration of the ultrasonic probe according to the third embodiment of the invention. The ultrasonic probe shown in FIG. 12 has a piezoelectric transducer 101. The piezoelectric transducer 101 has a rectangular solid shape. The piezoelectric transducer 101 comprises a large number of (for example, 128 to 256) strip-shaped piezoelectric elements 102.

Each of the piezoelectric elements 102 has a piezoelectric material 102a, earth electrode 102c (first electrode), and signal electrode 102b (second electrode), and each of the signal electrode 102b and the earth electrode 102c is provided on either end face of the piezoelectric material 102a in a radial direction. On a surface of the earth electrode 102c, the audio matching layer 103 for matching the audio impedance is provided.

The same materials as those for the piezoelectric material 2a, signal electrode 2b and earth electrode 2c, and audio matching layer 3 are used for the piezoelectric material 102a, signal electrode 102b and earth electrode 102c, and audio matching layer 103.

As shown in FIG. 12, at the earth electrode 102c side of the piezoelectric transducer 101, and audio lens 104 is provided through the audio matching layer 103. At the signal electrode 102b side of the piezoelectric transducer 101, a block-like backing material 105 is jointed through epoxy-based resin 114. A material such as the rubber having the good sound absorption performance is used for the backing material 105.

An FPC 106 (first conductive substrate) is provided parallel on one side face of the piezoelectric transducer 101 with a slight interval, or provided such that the composition angle, θ, is approximately 90 degrees, and an FPC 107 (second conductive substrate) is provided parallel on the other side face with a slight interval, or provided such that the composition angle, θ, is approximately 90 degrees.

The FPC 106 has a signal wiring 106a exposed to the piezoelectric transducer 101 side. The signal wiring 106a has electrical paths (refer to FIG. 4) of which the number is corresponding to the number of the piezoelectric elements 102. The FPC 107 has an earth wiring 107a exposed to the piezoelectric transducer 101 side. The earth wiring 107a has the electrical paths (refer to FIG. 4) of which the number is corresponding to the number of the piezoelectric elements 102.

In a corner portion 110a formed by the piezoelectric transducer 101 and the FPC 107, fillet 109a formed by a soldering material (conductive material) is arranged. The soldering material 109 in the first corner portion 110a positioned at the earth electrode 102c side electrically connects the earth wiring 107a to the earth electrode 102c.

A fillet 109b formed by the soldering material is arranged in a corner portion 110b formed by the piezoelectric transducer 101 and the FPC 106. The fillet 109b in the second corner portion 110b positioned at the signal electrode 102b side electrically connects the signal wiring 106a to the signal electrode 102b.

The fillets 109a, 109b generate a tensile stress that is stronger than a shearing stress on the jointed stress that is stronger than a shearing stress on the jointed faces with the piezoelectric transducer 101 or the FPCs 106, 107, and thus improve the jointing strength on the jointed faces.

A nonconductive adhesive 111 (nonconductive material) for insulating the signal electrode 102b from the earth electrode 102c is interposed between the piezoelectric transducer 101 and the FPC 106. The nonconductive adhesive 111 also acts to temporarily fix the piezoelectric transducer 101 to the FPCs 106, 107 in the fabrication process of the ultrasonic probe.

Rear anchor portions of the FPCs 106, 107 are connected to the main body of the ultrasonic diagnostic equipment (not shown) disposed at the backing material 105 side through the connector (not shown).

In the configured ultrasonic probe, the FPCs 106, 107 are disposed parallel on the side faces of the piezoelectric transducer 101, and the fillets 109a, 109b are formed in the corner portions 110a, 110b formed by the piezoelectric transducer 101 and the FPCs 106, 107, thereby the signal electrode 102b is connected electrically to the signal wiring 106a, and the earth electrode 102c is connected to the earth wiring 107a.

Thus, since the FPCs 106, 107 can be maintained flat without requiring bending the FPCs 106, 107 in the vicinity of the piezoelectric transducer 101 to connect the piezoelectric transducer 101 to the FPCs 106, 107, the unnecessary load is not applied, therefore the jointed strength of the piezoelectric transducer 101 with the FPCs 106, 107 is improved.

Figure 13:
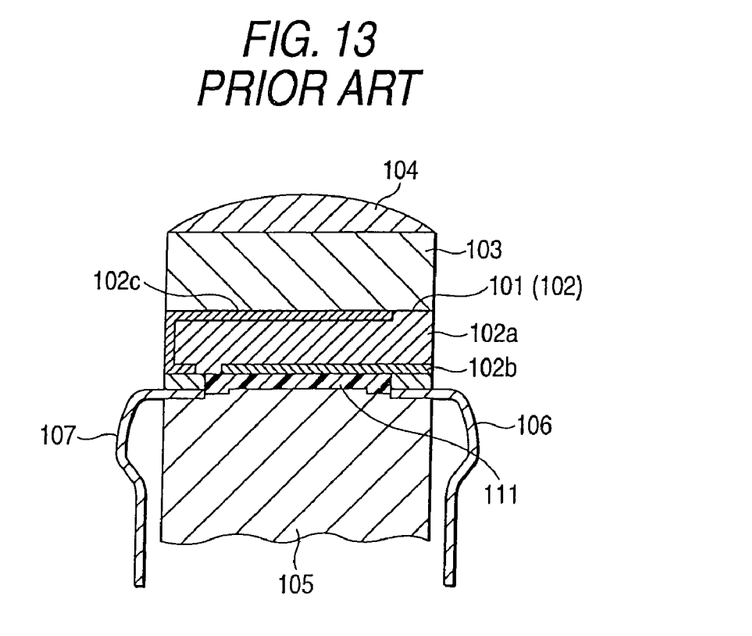
FIG. 13 is a cross sectional view showing a conventional ultrasonic probe.

FIG. 13 is a view showing a related art for illustrating the jointed strength in FIG. 12, and a same symbol is marked to a same functional part as in FIG. 12, and detailed description of the art is omitted.

While soldering strength is 0.22 N/mm in the art shown in FIG. 13, the strength is 1.62 N/mm in the embodiment shown in FIG. 12, which shows improvement of the soldering strength. Also, while the bending stress of the FPC is 300 $N/mm^2$ in the art shown in FIG. 13, it is approximately 0 $N/mm^2$ in the embodiment shown in FIG. 12, which shows substantially no load is applied.

The invention, which is not limited to the above embodiments, can be altered variously within a scope without going beyond the gist of the invention.

Additional advantages and modifications will readily occur to those skilled in the art. Therefore, the invention in its broader aspects is not limited the specific details and representative embodiments shown and described herein. Accordingly, various modifications may be made without departing from the spirit or scope of the general inventive concept as defined by the appended claims and their equivalents.

What is claimed is:

1. An ultrasonic probe, comprising:
   a piezoelectric transducer configured to send and to receive an ultrasonic wave;
   a conductive substrate for applying current to the piezoelectric transducer, wherein the conductive substrate is arranged oppositely to a side face of the piezoelectric transducer and has an end portion that is arranged outside of the side face of the piezoelectric transducer, the substrate further comprising a signal wiring and an earth wiring;
   first and second conductive materials arranged in first and second corner portions formed by the piezoelectric transducer and the conductive substrate, the conductive material electrically connecting the piezoelectric transducer to the conductive substrate; and
   a nonconductive material arranged on the side face of the piezoelectric transducer between the first and second corner portions, the nonconductive material insulating the first corner portion from the second corner portion.

2. The ultrasonic probe according to claim 1, wherein
   either one of the wirings is electrically connected to a first electrode disposed on a surface side of the piezoelectric transducer by the conductive material arranged in the first corner portion formed by a surface of the piezoelectric transducer and the conductive substrate, and
   the other wiring is electrically connected to a second electrode formed on a back side of the piezoelectric transducer by the conductive material arranged in the second corner portion formed by the back of the piezoelectric transducer and the conductive substrate.

3. The ultrasonic probe according to claim 1,
   wherein the conductive material is coated by a second nonconductive material.

4. The ultrasonic probe according to claim 1, wherein a face of the conductive substrate at a side of the piezoelectric transducer is disposed on a plane equal to a side face of the piezoelectric transducer or a plane spaced from the piezoelectric transducer.

5. The ultrasonic probe according to claim 1, wherein the conductive substrate is flat in the vicinity of the piezoelectric transducer.

6. The ultrasonic probe according to claim 1, wherein the conductive material is disposed in a fillet pattern.

7. The ultrasonic probe according to claim 1, wherein the conductive substrate comprises:
   a first substrate having the signal wiring for applying current to the piezoelectric transducer; and
   a second substrate having the earth wiring for connecting to the piezoelectric transducer,
   wherein the first substrate is arranged oppositely to a first side face of the piezoelectric transducer,
   the second substrate is arranged oppositely to a second side face of the piezoelectric transducer,
   the earth wiring is electrically connected to a first electrode disposed on a first main-face side of the piezoelectric transducer by the first conductive material arranged in the first corner portion formed by the first substrate,
   and the signal wiring is electrically connected to a second electrode formed on a second main-face side of the piezoelectric transducer by the second conductive material arranged in the second corner portion formed by the second substrate.

8. The ultrasonic probe according to claim 7, wherein the conductive material is coated by a second nonconductive material.

9. The ultrasonic probe according to claim 7, wherein faces of the first and second substrates at a side of the piezoelectric transducer are disposed on a plane equal to the side of the piezoelectric transducer or a plane spaced from the side of the piezoelectric transducer.

10. The ultrasonic probe according to claim 7, wherein the first and second conductive materials are disposed in a fillet pattern.

* * * * *